US011619597B2

(12) United States Patent
Schlecht et al.

(10) Patent No.: US 11,619,597 B2
(45) Date of Patent: Apr. 4, 2023

(54) DUAL ROBOT CONTROL SYSTEMS FOR NON-DESTRUCTIVE EVALUATION

(71) Applicant: Illinois Tool Works Inc., Glenview, IL (US)

(72) Inventors: Joseph Schlecht, Edina, MN (US); Caleb N. Hay, Eden Prairie, MN (US); Jackson Turner, Plymouth, MN (US); Sean Lin, Hopkins, MN (US); Sean M. Anderson, Big Lake, MN (US); Kirk Guillaume, Brooklyn Park, MN (US); Matthew James Johnson, Rogers, MN (US)

(73) Assignee: Illinois Tool Works Inc., Glenview, IL (US)

( * ) Notice: Subject to any disclaimer, the term of this patent is extended or adjusted under 35 U.S.C. 154(b) by 301 days.

(21) Appl. No.: 16/885,115

(22) Filed: May 27, 2020

(65) Prior Publication Data

US 2021/0372952 A1    Dec. 2, 2021

(51) Int. Cl.
*G01N 23/00* (2006.01)
*G01N 23/083* (2018.01)
(Continued)

(52) U.S. Cl.
CPC ............ *G01N 23/083* (2013.01); *B25J 9/045* (2013.01); *B25J 9/1669* (2013.01); *B25J 13/081* (2013.01);
(Continued)

(58) Field of Classification Search
None
See application file for complete search history.

(56) References Cited

U.S. PATENT DOCUMENTS

| 6,104,780 A | 8/2000 | Hanover et al. |
| 6,200,024 B1 | 3/2001 | Negrelli |

(Continued)

FOREIGN PATENT DOCUMENTS

| CA | 2400406 A1 | 8/2001 |
| EP | 2119397 A1 | 11/2009 |

(Continued)

OTHER PUBLICATIONS

International Search Report and Written Opinion of International Application No. PCT/US2021/026168, dated Jul. 21, 2021, 10 pp.

*Primary Examiner* — Hoon K Song
(74) *Attorney, Agent, or Firm* — Shumaker & Sieffert, P.A.

(57) ABSTRACT

A system for non-destructive evaluation of an object uses a spherical coordinate system to control two robotic arms. In some examples, the system includes a radiation source coupled to one robotic arm, a radiation detector coupled to the other robotic arm; and a control unit configured to determine, based on input, a first position located on a first surface of a first sphere within the spherical coordinate system; determine, based on the input, a second position located on a second surface of a second sphere within the spherical coordinate system, wherein the second position is located opposite a midpoint of the spherical coordinate system from the first position; and control a motion of the source robotic arm and the detector robotic arm such that the radiation source and the radiation detector move to different ones of the first position and the second position.

18 Claims, 8 Drawing Sheets

(51) Int. Cl.
  *G06T 7/70* (2017.01)
  *B25J 9/04* (2006.01)
  *B25J 9/16* (2006.01)
  *B25J 13/08* (2006.01)
  *B25J 15/00* (2006.01)
  *B25J 19/02* (2006.01)
  *G01N 23/046* (2018.01)
  *G01N 23/18* (2018.01)
  *G06T 5/50* (2006.01)

(52) U.S. Cl.
  CPC ........... *B25J 15/0019* (2013.01); *B25J 19/02* (2013.01); *G01N 23/046* (2013.01); *G01N 23/18* (2013.01); *G06T 5/50* (2013.01); *G06T 7/70* (2017.01); *G06T 2207/10116* (2013.01); *G06T 2207/20221* (2013.01)

(56) References Cited

U.S. PATENT DOCUMENTS

| | | | |
|---|---|---|---|
| 6,582,121 B2 | 6/2003 | Crain et al. | |
| 6,842,502 B2 | 1/2005 | Jaffray et al. | |
| 7,254,211 B2 | 8/2007 | Hunt et al. | |
| 7,627,083 B2 | 12/2009 | Ross et al. | |
| 7,657,304 B2 | 2/2010 | Mansfield et al. | |
| 7,922,391 B2 | 4/2011 | Essenreiter et al. | |
| 8,135,111 B2 | 3/2012 | Jaffray et al. | |
| 8,774,349 B2 | 7/2014 | Muenker et al. | |
| 9,459,217 B2 | 10/2016 | Wang et al. | |
| 10,475,240 B2 | 11/2019 | Evans et al. | |
| 2004/0024300 A1 | 2/2004 | Graf | |
| 2009/0116620 A1* | 5/2009 | Kato | G03B 42/02 378/167 |
| 2011/0069818 A1* | 3/2011 | Muller | A61B 6/4458 378/197 |
| 2015/0150525 A1 | 6/2015 | Navab et al. | |
| 2015/0216498 A1 | 8/2015 | Schulze et al. | |
| 2019/0000407 A1* | 1/2019 | Muller | A61B 6/547 |

FOREIGN PATENT DOCUMENTS

| | | |
|---|---|---|
| JP | 2006084467 A | 3/2006 |
| JP | 4424560 B2 | 3/2010 |
| JP | 2010127810 A | 6/2010 |
| JP | 2015525665 A | 9/2015 |
| WO | 2006042211 A2 | 4/2006 |
| WO | 2009121822 A1 | 10/2009 |
| WO | 2010086706 A1 | 8/2010 |
| WO | 2019110024 A1 | 6/2019 |

* cited by examiner

DUAL ROBOT CONTROL SYSTEMS FOR NON-DESTRUCTIVE EVALUATION

TECHNICAL FIELD

This disclosure relates to non-destructive evaluation of objects.

BACKGROUND

X-ray digital radiography (DR) is a commonly used non-invasive and non-destructive imaging technique using digital x-ray detectors, such as flat-panel detectors, charge-coupled device (CCD) cameras, or complementary metal-oxide-semiconductor (CMOS) cameras, or linear diode arrays (LDAs). X-ray computed tomography (CT) is a procedure that uses computer-processed x-rays radiographs acquired at different view angles to produce 3D images of an object. A tomographic image of an object is an image of a conceptually two-dimensional "slice" of the object. A computing device may use the tomographic images of the object to generate a 3-dimensional image of the object. X-ray CT may be used for industrial purposes to conduct non-destructive evaluation of objects.

SUMMARY

In general, this disclosure relates to non-destructive evaluation (NDE), such as industrial x-ray radiography, computed tomography (CT) and metrology. This disclosure describes an apparatus and method that may enable non-destructive evaluation of an object from many different perspectives while also simplifying for a user the alignment of a radiation source and a detector. The techniques of this disclosure provide an instrumentation design, user control mechanism, and software algorithm for the apparatus. The apparatus may be used for NDE of naturally occurring objects, such as rock core samples, as well as manufactured components and systems, such as metal casts, engine components, and complete engine units. The apparatus may comprise a radiation source, a radiation detector, and a sample manipulator, each with associated motion control systems. The sample manipulator may position samples so that radiographs can be obtained at different positions and viewing angles.

In one example, this disclosure describes a system for non-destructive evaluation of an object, including a first robotic ami; a radiation source coupled to the first robotic arm, the radiation source configured to emit radiation; a second robotic arm; radiation detector coupled to the second robotic arm, the radiation detector configured to measure the radiation emitted by the radiation source; a stage configured to support the object for non-destructive evaluation; and a control unit configured to: determine, based on input, a first position located on a first surface of a first sphere within a spherical coordinate system; determine, based on the input, a second position located on a second surface of a second sphere within the spherical coordinate system, wherein the second position is located opposite a center of the spherical coordinate system from the first position; and control a motion of the first robotic arm and the second robotic arm such that the radiation source and the radiation detector move to different ones of the first position and the second position.

In another example, this disclosure describes a non-transitory computer-readable data storage medium having instructions stored thereon that, when executed by a system for non-destructive evaluation of an object placed on a stage, cause the system to: determine, based on input, a first position located on a first surface of a first sphere within a spherical coordinate system; determine, based on the input, a second position located on a second surface of a second sphere within the spherical coordinate system, wherein the second position is located opposite a center of the spherical coordinate system from the first position; and control a motion of a first robotic ann. and a motion of a second robotic arm such that a radiation source and a radiation detector move to different ones of the first position and the second position.

In another example, this disclosure describes a method including: determining, based on input into a system for non-destructive evaluation of an object placed on a stage, a first position located on a first surface of a first sphere within a spherical coordinate system; determining, based on the input, a second position located on a second surface of a second sphere within the spherical coordinate system, wherein the second position is located opposite a center of the spherical coordinate system from the first position; and controlling a motion of a first robotic arm and a motion of a second robotic ami such that a radiation source and a radiation detector move to different ones of the first position and. the second position.

The details of one or more examples are set forth in the accompanying drawings and the description below. Other features, objects, and advantages will be apparent from the description, drawings, and claims.

DETAILED DESCRIPTION

Figure 1:
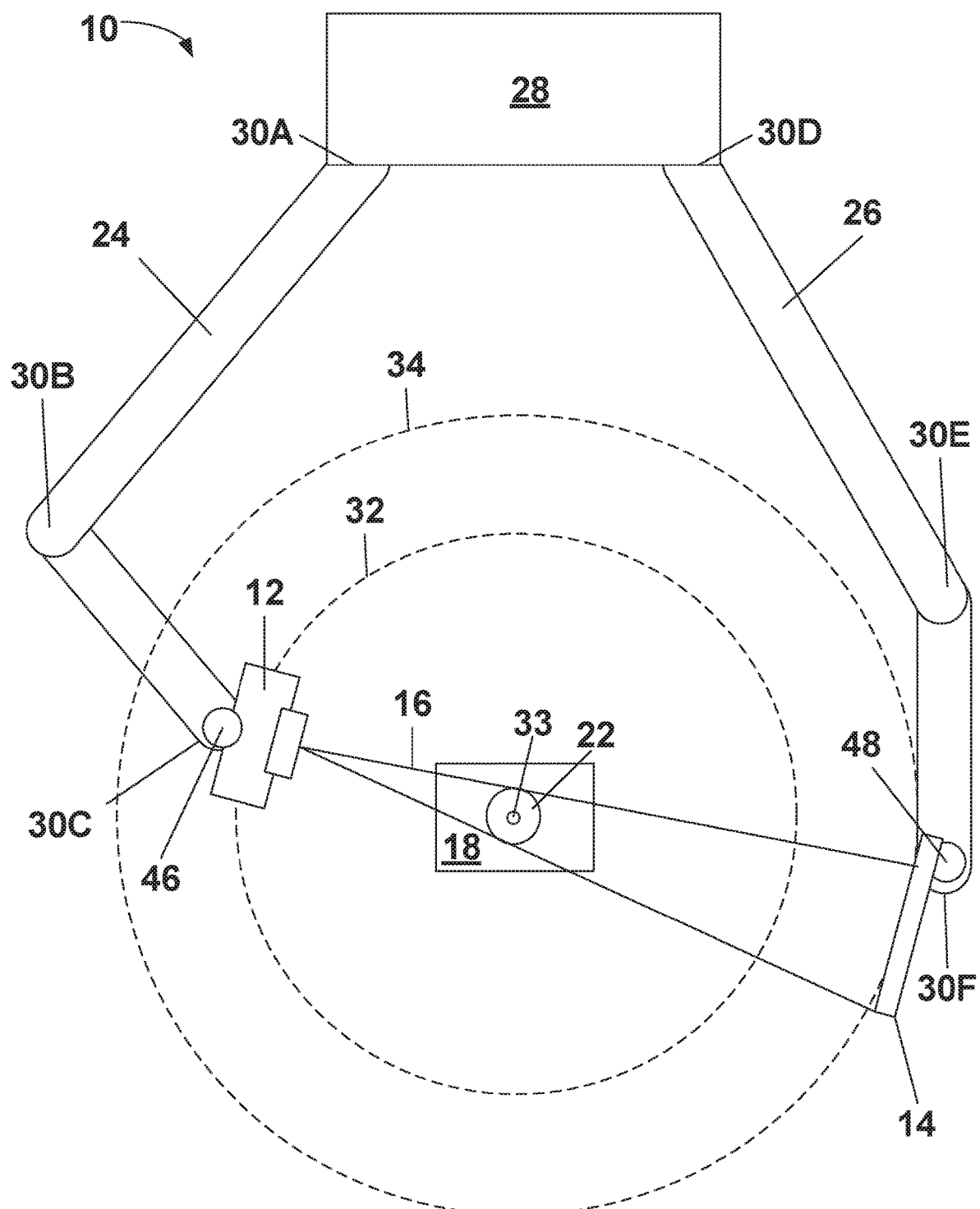
FIG. 1 is a schematic drawing of an example instrumental setup of a non-destructive evaluation (NDE) system, in accordance with one or more techniques of this disclosure.

Non-destructive evaluation (NDE) or non-destructive analysis (NDA) of an object may include non-invasively imaging, measuring, or otherwise evaluating two-dimensional or three dimensional structures. Some commonly used techniques for NDE in medical or industrial imaging include x-ray radiography and computed tomography (CT). One or more example techniques of this disclosure relate to industrial applications of x-ray CT or metrology. For example, FIG. 1 is a schematic drawing depicting an overhead view of an example instrumental setup, in accordance with one or more techniques of this disclosure. As shown in the example of FIG. 1, an NDE system 10, such as an industrial CT system, may include a radiation source 12 and a radiation detector 14. Radiation source 12 may emit electromagnetic radiation, such as x-ray beam 16. Hence, in some instances, this disclosure may refer to radiation source 12 or similar devices as "x-ray generators" In some examples, x-ray beam 16 may be cone-shaped. In other examples, x-ray beam 16 may be fan-shaped. In some examples, x-ray source 12 generates x-rays with an energy range of 20 keV to 600 keV. In other examples, x-ray source 12 may generate x-rays in other energy ranges. In other examples, beam 16 may include other frequencies of the electromagnetic spectrum, such as a gamma ray beam.

Samples may be mounted on a manipulator. In system 10, the manipulator may include a rotary stage 18 (i.e., a rotation stage) with an axis of rotation 20. The rotary stage 18 may he configured to carry and rotate a sample or object 22 and may be disposed between x-ray source 12 (i.e., an x-ray generator) and radiation detector 14. Consequently, radiographs may be acquired at different projection angles or perspectives as the sample is rotated in x-ray beam 16. Thus, in some examples where the manipulator includes a rotation stage 18, a computing system of system 10 may acquire radiographs at different detector positions for different rotation angles and may process the radiographs to assemble the radiographs into a 3-dimensional radiograph of the sample. In some examples, rotary stage 18 may include an 18-inch, nickel-plated, aluminum turn-table platter.

Radiation detector 14 may include a flat-panel x-ray detector (FPD), as shown in the example of FIG. 1. In other examples, radiation detector 14 may include a lens-coupled scintillation detector, a linear diode array (LDA), or another type of radiation detector. An FPD may include a layer of scintillation material, such as Cesium Iodide fabricated on amorphous silicon on a glass detector array. The scintillator layer absorbs x-rays and emits visible light photons that are, in turn, detected by a solid state detector, The detector pixel size may range from tens to hundreds of micrometers. In some examples where radiation detector 14 comprises a flat-panel x-ray detector, the pixel size of radiation detector 14 may be in the range of 25 micrometers to 250 micrometers. In some examples, the pixel size of radiation detector 14 may be in the range of approximately 25 micrometers to approximately 250 micrometers. Furthermore, the field of view of common commercial FPDs may range from approximately 100 mm to 500 mm. Commercial FPDs may be used in applications requiring large fields of view, High-resolution applications may require lens-coupled detectors that use an optical lens to relay emitted visible light to a detector, such as a charge-coupled device (CCD) or a complementary metal-oxide-semiconductor (CMOS) detector. In some examples, the lens may provide magnification in the range of 1× to 100×, thus making the effective pixel size between 0.1 to 20 micrometers. In some examples where radiation detector 14 comprises a lens-coupled detector, the pixel size of radiation detector 14 is in a range of 0.1 micrometers to 10 micrometers. Furthermore, in some examples where radiation detector 14 comprises a lens-coupled detector, the field of view may range from 0.2 mm to 25 mm.

A user of system 10 may be interested in capturing images (e.g., x-ray images) of a part, sample, or object 22 from multiple different angles for a thorough evaluation of its internal structure. Some traditional imaging systems may include components configured to maneuver either or both of radiation source 12 and/or detector 14 along generally linear axes. For example, a traditional imaging system may include rails, gears, and/or other mechanical components configured to linearly translate source 12 and/or detector 14 along orthogonal cartesian axes, such as a horizontal axis (e.g., toward and away from object 22) and/or a vertical axis. In these examples, a user may need to manually re-orient object 22 with respect to source 12 and detector 14 in order to image object 22 from different rotational angles. This may be difficult or inconvenient when object 22 is relatively large, bulky, and/or heavy. Accordingly, some other traditional imaging systems include "C. Arm" systems, wherein each of source 12 and detector 14 are mounted onto opposite ends of a machine shaped like the letter "C." In some examples, the C-shaped machine then rotates around object 22 to image the object from multiple angles. A typical example of this type of C-arm system includes a dentist's x-ray machine, which rotates around the head of a patient in order to image the patient's teeth from multiple perspectives. In other examples, the object undergoing evaluation may be placed on a rotary stage, which may rotate the object relative to the radiation source and detector. However, since radiation source 12 and detector 14 are both rigidly coupled to the same structure, typical C-arm systems are likewise limited in their mobility, in that the stage and/or the C arm may rotate about only a single vertical or horizontal axis, e.g., they may only image an object 22 along an axis that is directly orthogonal (e.g., perpendicular) to the axis of rotation of the C-arm structure.

More advanced imaging systems, such as NDE system 10 shown in FIG. 1, may include two robotic arms 24, 26. Radiation source 12 and detector 14 are mounted onto distal ends of different ones of robotic arms 24, 26, which may then be maneuvered independently of each other in order to image object 22 from multiple angles along multiple different axes of rotation. Each of robotic arms 24, 26 may include one or more joints 30A-30F (collectively, "joints 30") defining multiple degrees of freedom within three-dimensional space within which to image object 22. For example, each robotic arm may include six joints. However, these additional degrees of freedom provide both advantages and disadvantages. Although the robotic arms 24, 26 may allow for improved imaging of object 22, the dual robotic arms 24, 26 of systems such as system 10 may lend additional (e.g., excessive) complexity to the imaging process. For example, in order to successfully image or measure object 22, radiation source 12 and detector 14 must be aligned directly opposite one another from object 22. Since each robotic arm 24, 26 may be manually operated independently of the other robotic arm (e.g., via a graphical user interface; a variable-speed, multi-directional joystick; or other user-input device), some dual-robotic-arm-type systems may require significant trial-and-error and/or manual position determinations in order to properly align radiation source 12, object 22, and radiation detector 14.

In some examples in accordance with this disclosure. NDE system 10 includes a control unit, such as image acquisition system 28, configured to receive input indicating at least a desired imaging angle (e.g., imaging perspective) and a desired imaging magnification, and then automatically align source 12, object 22, and detector 14 based on the user input. For example, image acquisition system 28 may determine, based on the desired imaging angle and/or the desired imaging magnification, a source position and a detector position, and then control the joints of the robotic arms to place the source and detector in their respective positions.

Image acquisition system 28 may comprise a computing system. Example types of computing systems may include personal computers, server computers, mainframe computers, laptop computers, special-purpose computers, and so on. Image acquisition system 28 may implement a computer-controlled image-acquisition procedure comprising (e.g., consisting of) determining, based on input, a source position and a detector position, and then controlling any of a number of controllable mechanical components of system 10 to move rotate and or translate) radiation source 12 toward the source position and radiation detector 14 toward the detector position. In some examples in accordance with this disclosure, image acquisition system 28 may determine (e.g., generate or calculate) the source position and the detector position according to locations defined by a spherical coordinate system, such that the source position is located at a point on the surface of a first imaginary sphere 32 and the detector position is located at a point on the surface of a second imaginary sphere 34, wherein the two imaginary spheres are concentric, e.g., sharing a common center 33 with the spherical coordinate system.

Figure 2:
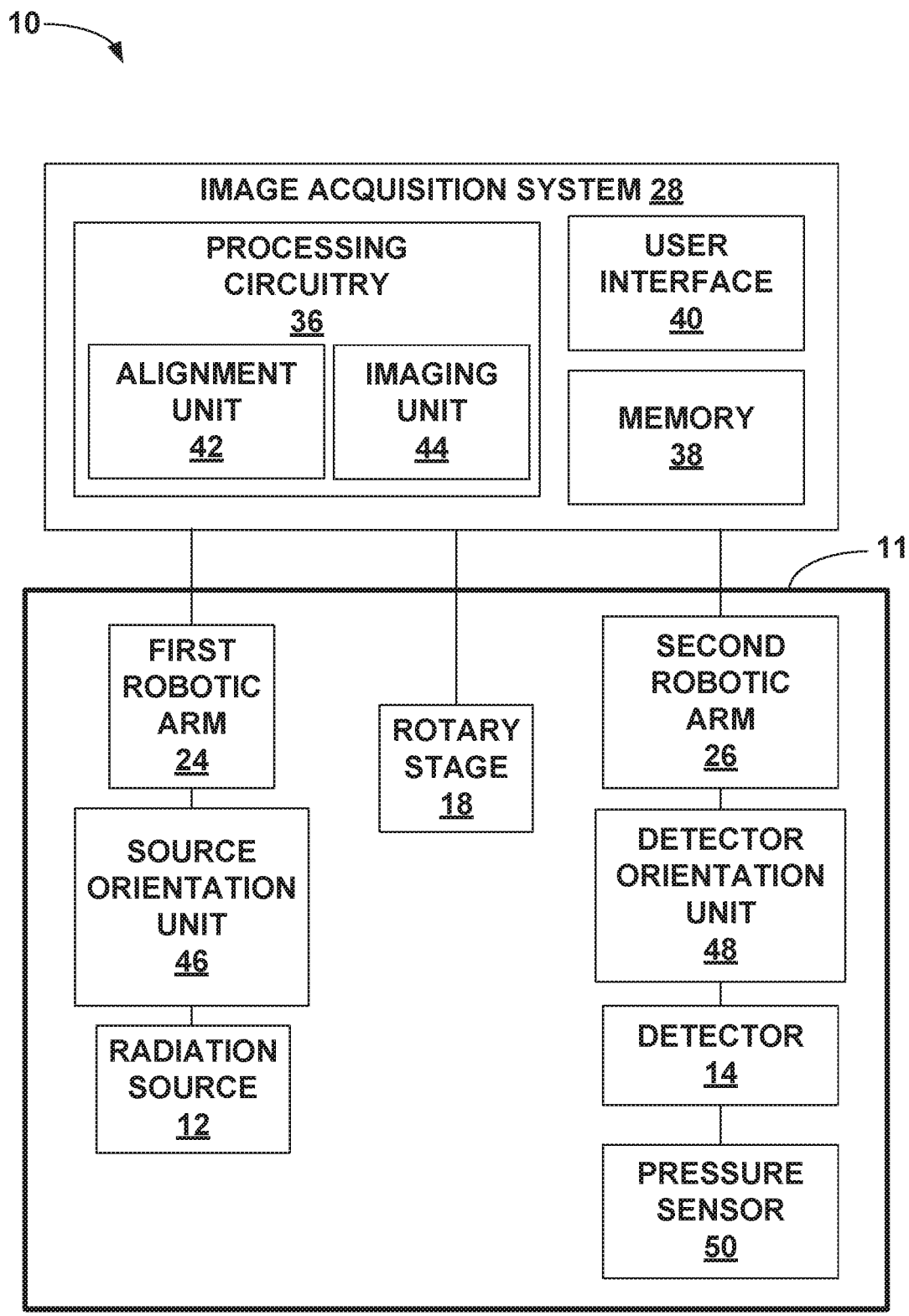
FIG. 2 is a conceptual block diagram of some example components of the instrumental setup of FIG. 1.

FIG. 2 is a conceptual block diagram depicting some example components of system 10 of FIG. 1, in accordance with techniques of this disclosure. In the example of FIG. 2, system 10 includes housing 11, radiation source 12, radiation detector 14, rotary stage 18, first robotic arm 24, second robotic arm 26, image acquisition system 28, orientation units 46 and 48, and pressure sensor 50. In other examples, system 10 may include more, fewer, or different components.

In some examples, one or more components of system 10 are contained within housing 11. Housing 11 may include a radiation shielding, such as protective shielding against radiation energies of up to 240 kilovolts (kV) constant potential. In some examples, the enclosure may include dimensions of about 158 inches wide by about 98 inches deep by about 123 inches tall (e.g., about 401 cm wide by about 249 cm deep by about 312 cm tall). Housing 11 may be composed of lead and/or steel components, defining a motorized sliding access door for accessing rotary stage 18 to place an object 22 for non-destructive evaluation (e.g., imaging or metrology). Housing 11 may further include interior lighting and a cable access port with a cover, as well as an "X-Ray On" warning light, Image acquisition system 28 is configured to receive input indicating at least a desired imaging angle and a desired imaging magnification, and then automatically align source 12, object 22, and detector 14 based on the input. For example, received input may include direct (e.g., real-time) user input, or in some examples, a set of predetermined instructions stored within a file that is imported or otherwise received by image acquisition system 28.

Image acquisition system 28 may comprise a computing system. For example, image acquisition system 28 may implement a computer-controlled image acquisition procedure that includes determining, based on the received input, a source position and a detector position, and then controlling any of a number of controllable mechanical components of system 10 to move (e.g., rotate and/or translate) radiation source 12 toward the determined source position and detector 14 toward the determined detector position. Image acquisition system 28 may determine (e.g., receive, generate, or calculate) the source and detector positions within a spherical coordinate system, such that the source position is located at a point on the surface of a first imaginary sphere and the detector position is located at a point on the surface of a second imaginary sphere, wherein the two imaginary spheres are concentric.

As shown in FIG. 2, image acquisition system 28 includes at least processing circuitry 36, memory 38, and user interface 40. Processing circuitry 36 is configured to execute alignment unit 42 and imaging unit 44. Alignment unit 42 is configured to receive user input, via user interface (UI) 40 indicating a desired imaging perspective (e.g., imaging angle) and/or a desired imaging magnification. User interface 40 may include any suitable user input/output devices, such as a graphical user interface, an interactive voice interface, a command line interface, or the like. Based on the user input, alignment unit 42 may determine a source position and a detector position to align radiation source 12 and radiation detector 14 on opposite sides of the center of a spherical coordinate system centered at center 33. In the example shown in FIGS. 1 and 3, center 33 is located at a pre-determined distance above rotary stage 18, e.g., along rotary axis 20 (FIG. 1). However, as detailed further below, image acquisition system 28 may move (e.g., re-define a location of) center 33 to any arbitrary position based on received input.

Additionally or alternatively, alignment unit 42 may determine, based on the received input, a source orientation and/or a detector orientation. For example, alignment unit 42 may control source orientation unit 46 and/or detector orientation unit 48 to orient radiation source 12 and/or radiation detector 14, respectively, such that radiation source 12 and radiation detector 14 are "aimed" at one another from their respective positions, e.g., such that radiation beam 16 is aimed toward detector 14 from source position 12. For example, source orientation unit 46 may be an example of one of joints 30 (e.g., joint 30C of FIG. 1) of robotic arm 24, such as a ball-and-socket-type joint, configured to rotate to change an orientation of radiation source 12. Similarly, detector orientation unit 48 may be an example of one of joints 30 (e.g., joint 30F of FIG. 1) of robotic arm 26, such as a ball-and-socket-type joint, configured to rotate to change an orientation of radiation detector 14. In other examples, each of source orientation unit 46 and detector orientation unit 48 may include two or more joints 30 configured to act or move in concert (e.g., under the control of alignment unit 42) to mimic the functionality of a single ball-and-socket-type joint.

Once alignment unit 42 has positioned and/or oriented both radiation source 12 and radiation detector 14, imaging unit 44 may non-destructively evaluate (e.g., irradiate to image or measure) an object 22 placed on rotary stage 18, by causing radiation source 12 to emit radiation beam 16 that passes through object 22 and contacts a surface of radiation detector 14.

In some examples, radiation detector 14 includes a protective plate having at least one pressure sensor 50 configured to disable the motion of robotic arm 26 in response to pressure sensor 50 detecting contact with another item, such as object 22, an interior surface of housing 11, radiation source 12, or robotic arm 24. For example, for some relatively larger or irregularly shaped objects 22, a movement of robotic arm 26 may cause radiation detector 14 to contact part of object 22. In these examples, pressure sensor 50 detects the physical contact with object 22, causing image acquisition system 28 to immediately terminate further motion of robotic arm 26, thereby reducing or preventing damage to object 22. Pressure sensor 50 may include a sensing plate that is highly transparent to radiation beam 16 and may trigger a shutdown of robotic arm 26 with a reaction time on the order of milliseconds.

Figure 3:
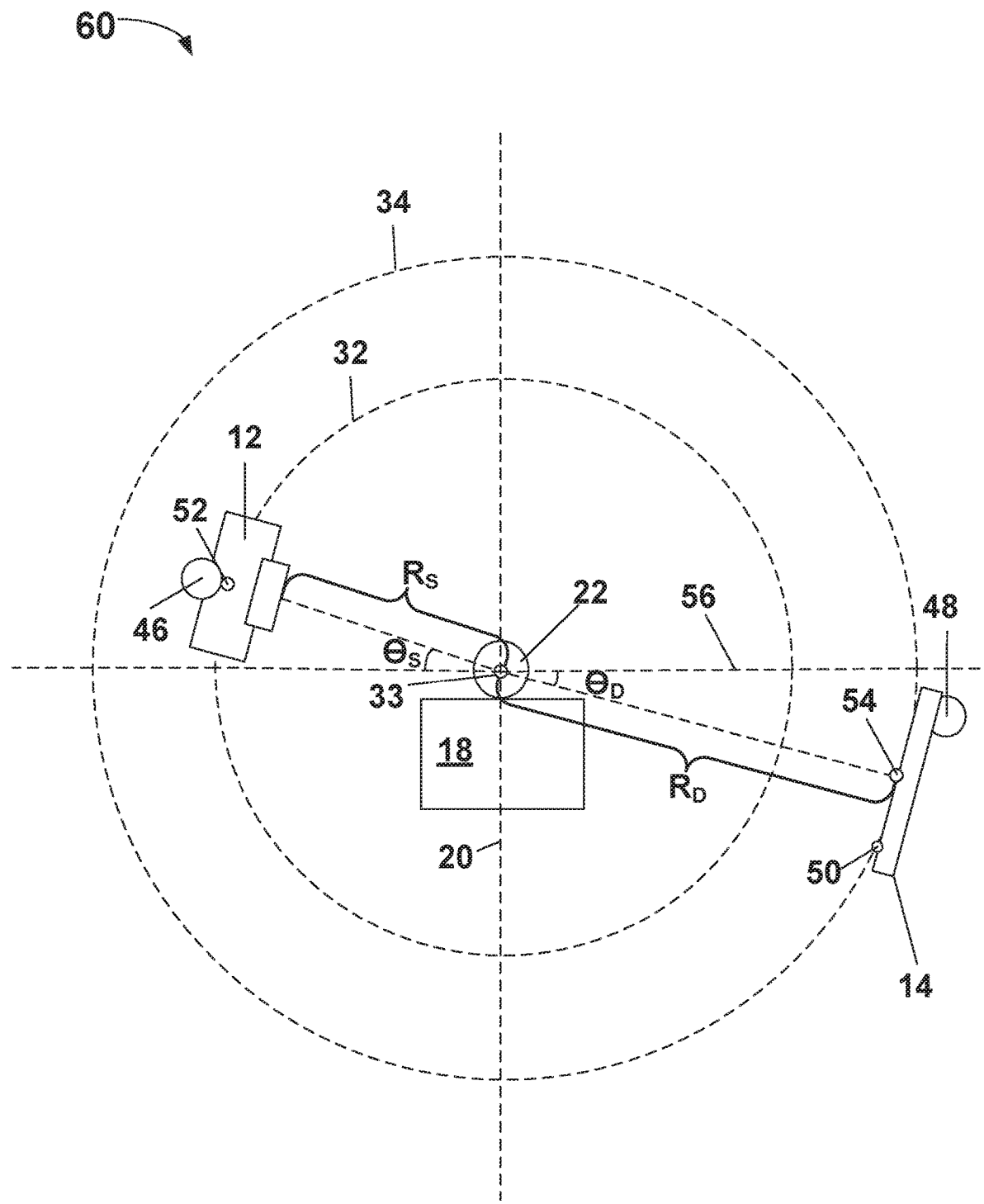
FIG. 3 is a conceptual side view of an example coordinate system for use by the NDE system of FIG. 1 to align a radiation source and a radiation detector, in accordance with one or more techniques of this disclosure.

FIGS. 3-6 are conceptual diagrams of various example coordinate systems that an NDE system (e.g., alignment unit 42 of image acquisition system 28 of NDE system 10 of FIG. 2) may use to calculate or determine at least a source position 52 for a radiation source 12 and a detector position 54 for a radiation detector 14. For example, FIG. 3 depicts a conceptual side view of an example spherical coordinate system 60 centered at center 33.

Radiation source 12 is located at a source position 52 located at a point in space defined by spherical coordinate system 60. For example, alignment unit 42 may define a first imaginary sphere 32 located within spherical coordinate system 60, e.g., centered at center 33 of coordinate system 60. Alignment unit 42 may then determine (e.g., calculate and/or assign) source position 52 to be located at a point on the surface of the first imaginary sphere 32. For example, source position 52 may be defined by three spherical coordinates, e.g., a radius R, an elevation angle θ (theta), and an azimuth angle φ (phi, shown in FIG. 4). As shown in FIG. 3, source position 52 is located at an elevation angle $\theta_S$ above horizontal plane 56 passing through center 33 of coordinate system 60. Source position 52 is located at a distance from center 33 measured by source radius $R_S$, which defines the radius of first imaginary sphere 32.

Similarly, radiation detector 14 is located at a detector position 54 located at a point in space defined by spherical coordinate system 60. For example, alignment unit 42 may define a second imaginary sphere 34 located within spherical coordinate system 60, e.g., centered at center 33 of coordinate system 60. Alignment unit 42 may then determine (e.g., calculate and/or assign) detector position 54 to be located at a point on the surface of the second imaginary sphere 34. For example, detector position 54 may be defined by three spherical coordinates: a radius R, an elevation angle theta θ, and an azimuth angle φ (phi, shown in FIG. 4). As shown in FIG. 3, detector position 54 is located at an elevation angle $\theta_D$ below horizontal plane 56, wherein detector elevation angle $\theta_D$ is equal and opposite to source elevation angle $\theta_S$. Detector position 54 is located at a distance from center 33 measured by detector radius $R_D$, which defines the radius of second imaginary sphere 34.

In some examples, alignment unit 42 is configured to receive further user input, e.g., via user interface 40, indicating a desired image magnification for imaging of an object 22 placed on stage 18. Alignment unit 42 determines values for source radius $R_S$ and detector radius $R_D$ based on the desired image magnification, wherein the magnification M is equal to the sum of the detector radius and the source radius divided by the source radius, e.g.:

$$M = \frac{(R_D + R_S)}{R_S}$$

Once alignment unit 42 has determined a source position 52 and a detector position 54, alignment unit 42 controls robotic arms 24, 26, to move radiation source 12 to source position 52 and radiation detector 14 to detector position 54. In some examples, robotic arm 24 may be configured to move radiation source 12 from a current source position to intended source position 52 according to the defined imaginary sphere 32. For example, robotic arm 24 may first move radiation source 12 radially outward or inward from a current source radius to the intended source radius $R_S$, and then rotate robotic arm 24 (e.g., via joints 30) such that radiation source 12 moves along the surface of imaginary sphere 32 toward intended source position 52. Similarly, robotic arm 26 may be configured to move radiation detector 14 from a current detector position to intended detector position 54 according to the defined imaginary sphere 34. For example, robotic arm 26 may first move radiation detector 14 radially outward or inward from a current detector radius to the intended detector radius $R_D$, and then rotate robotic arm 26 (e.g., via joints 30) such that radiation detector 14 moves along the surface of imaginary sphere 34 toward intended detector position 54.

In another example, rather than separately controlling a source radius and a source angle, alignment unit 42 may define a series of intermediate waypoints between the current source position and the desired source position. The set of waypoints may approximate a curve or arc between the current source position and the desired source position, such that each subsequent waypoint defines an incremental change in both radius and angle from center 33. Alignment unit 42 may then control joints 30 of robotic arm 24 such that radiation source 12 follows the arc defined by the waypoints to reach the intended source position.

Similarly, alignment unit 42 may define a series of intermediate waypoints between the current detector position and the desired detector position. The set of waypoints may approximate a curve or arc between the current detector position and the desired detector position, such that each subsequent waypoint defines an incremental change in both radius and angle from center 33. Alignment unit 42 may then control joints 30 of robotic arm 26 such that radiation detector 24 follows the arc defined by the waypoints to reach the intended detector position.

Figure 4:
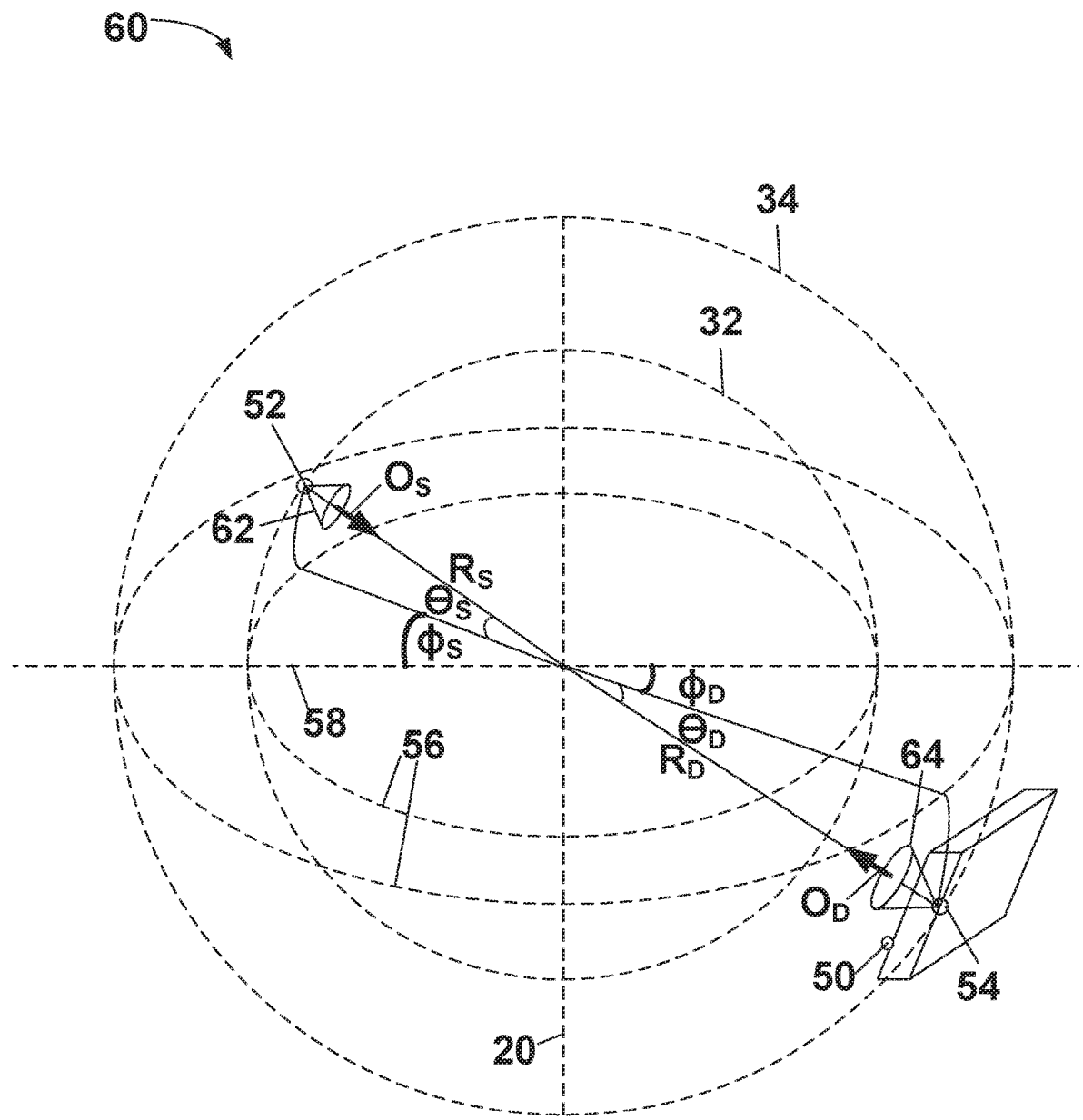
FIG. 4 is a conceptual perspective view of the example coordinate system of FIG.

FIG. 4 is a perspective view of the example spherical coordinate system 60 of FIG. 3. In addition to source elevation angle $\theta_S$, radiation source 12 may be described by source azimuth angle $\phi_S$ "above" horizontal axis 58 along horizontal plane 56. Accordingly, source position 52 may be described by the three spherical coordinates $(R_S, \theta_S, \phi_S)$. Image acquisition system 28 is configured to determine these three values of source position 52 based on user input, and control first robotic arm 24 to move radiation source 12 to be located at source position 52.

Similarly, in addition to detector elevation detector angle $\theta_D$, radiation detector 14 may be described by detector azimuth angle $\phi_D$ "below" horizontal axis 58 along horizontal plane 56, wherein detector azimuth angle $\phi_D$ of detector position 54 is equal and opposite to source azimuth angle $\phi_S$ of source position 52. Accordingly, detector position 54 may be described by the three spherical coordinates $(R_D, \theta_n, \phi_D)$. Image acquisition system 28 is configured to determine these three values of detector position 54 based on user input, and control second robotic arm 26 to move radiation detector 14 to be located at detector position 54.

In some examples, image acquisition system 28 is configured to determine and/or control a source orientation vector Os of radiation source 12 and/or a detector orientation vector $O_D$ of radiation detector 14. For example, image acquisition system 28 may control source orientation unit 46 (e.g., hinge 30C or a combination of two or more hinges 30) of robotic arm 24 to rotate radiation source 12 while radiation source 12 is located at source position 52. As shown in FIG. 4, as image acquisition system 28 controls the motion of source orientation unit 46, source orientation vector $O_S$ sweeps out a radiation cone 62 describing the possible paths from which radiation beam 16 (FIG. 1) may be emitted from radiation source 12. Radiation cone 62 may itself be described by two spherical coordinates within another imaginary sphere centered within orientation unit 46, for example, a source orientation azimuth angle and a source orientation elevation angle. In some examples, as described further below with respect to FIG. 6, radiation source 12 and radiation detector 14 may be configured to rotate about the axis or vector connecting them. In these examples, radiation cone 62 may be described by a third coordinate or variable defining its rotation about its own axis. Control over this third rotational variable may help enable "flat-field correction" of radiation beam 16 onto radiation detector 14, such as when radiation beam 16 does not inherently generate a rotationally symmetrical distribution of radiation onto detector 14.

Similarly, image acquisition system 28 may control detector orientation unit 48 (e.g., hinge 30F) of robotic arm 26, to rotate radiation detector 14 while radiation detector 14 is located at detector position 54. As shown in FIG. 4, as image acquisition system 28 controls the motion of orientation unit 48, detector orientation vector $O_D$ sweeps out a detector orientation cone 64 describing the possible orientations of a plane defined by a. surface of radiation detector 14, or equivalently, the possible orientations of orientation vector On tangent to the detector plane. Detector orientation cone 64 may itself be described by two spherical coordinates within another imaginary sphere centered within orientation unit 48, for example, a detector orientation azimuth angle and a detector orientation elevation angle. In some examples, as described further below with respect to FIG. 6, radiation source 12 and radiation detector 14 may be configured to rotate about the axis or vector connecting them. In these examples, radiation cone 64 may be described by a third coordinate or variable defining its rotation about its own axis. Control over this third rotational variable may help enable "flat-field correction" of radiation beam 16 onto radiation detector 14. such as when radiation beam 16 does not inherently generate a rotationally symmetrical distribution of radiation onto detector 14.

Figure 5:
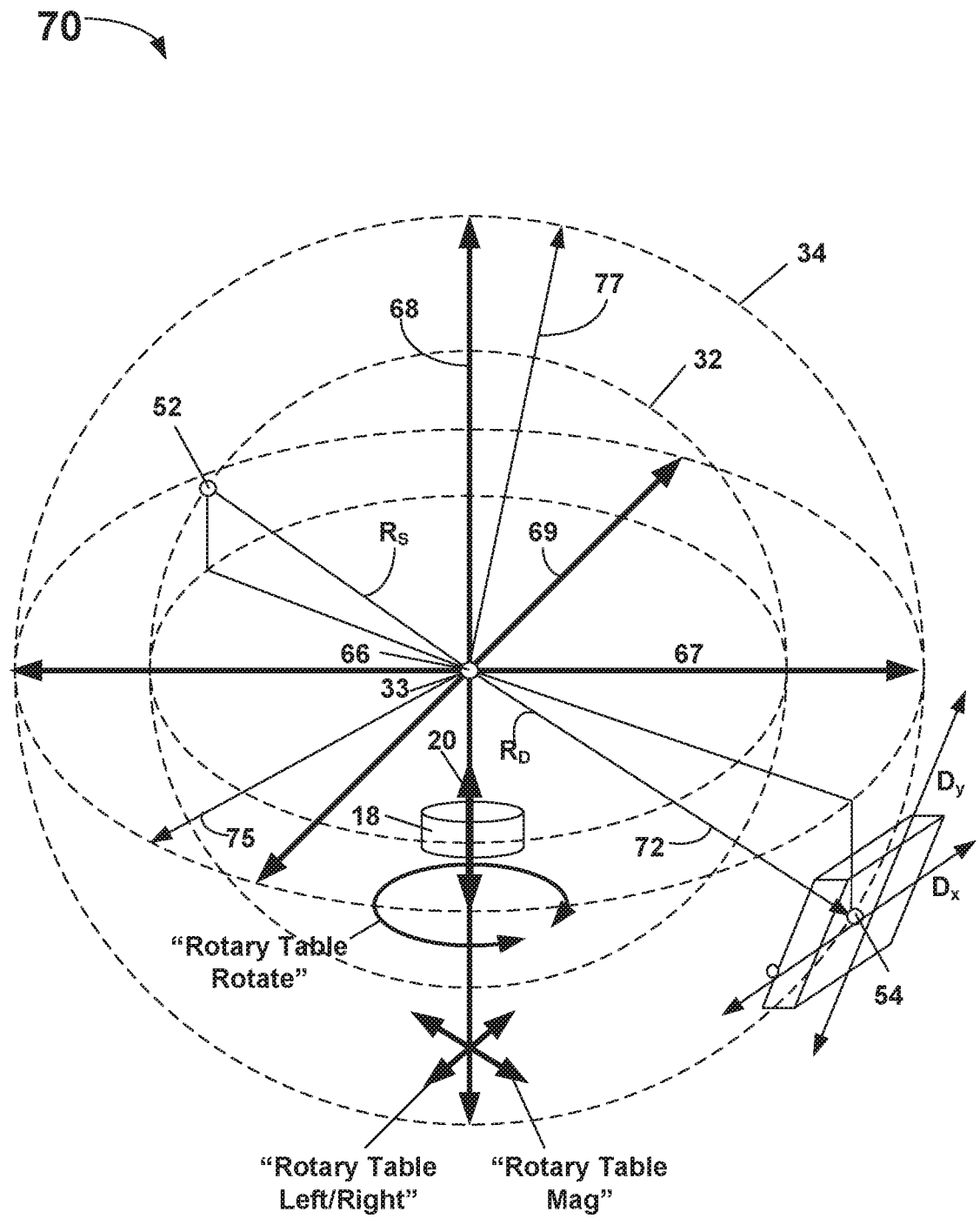
FIG. 5 is a conceptual perspective view of another example coordinate system in accordance with one or more techniques of this disclosure.

In total, as shown in FIG. 4, system 60 defines at least ten degrees of freedom three position axes and two orientation axes for each of radiation source 12 and radiation detector 14. As described above, imaging 60 may define a further two variables for the rotation of radiation source 12 and detector 14 about the axis connecting them. These twelve degrees of freedom may enable precise control over the imaging of object 22 from virtually any desired perspective and magnification. However, these twelve degrees of freedom are not intended to be limiting. Other configurations of imaging 60 may define fewer, additional, and/or different degrees of freedom, such as axes of translation and/or rotation defined by mechanical components of system 60. For example, FIG. 5 is a conceptual perspective view of another coordinate system 70 that an NDE system (e.g., alignment unit 42 of image acquisition system 28 of NDE system 10 of FIG. 2) may use to calculate or determine at least a source position 52 for a radiation source 12 and a detector position 54 for a radiation detector 14. Coordinate system 70 may be an example of spherical coordinate system 60 of FIGS. 3 and 4, or equivalently, spherical coordinate system 60 may be included within coordinate system 70. For example, similar to spherical coordinate system 60 of FIGS. 3 and 4, as shown in FIG. 5, coordinate system 70 includes a spherical coordinate system defining imaginary spheres 32, 34, upon which source position 52 and detector position 54 are located, respectively. However, coordinate system 70 may include at least 8 additional degrees of freedom not depicted in FIGS. 3 and 4.

For example, coordinate system 70 defines a cartesian coordinate system having an x-axis 67, a y-axis 68, and a z-axis 69 describing the position of a reference point, such as the center 33 of spherical coordinate system 70. That is, robotic arms 24 and 26 are commonly (e.g., as a combined unit) horizontally and vertically translatable along the reference-point x, y, and z axes to move radiation source 12 and detector 14 relative to rotary stage 18. In the example depicted in FIG. 5, center 33 of the spherical coordinate system [e.g., spherical point (0, 0, 0)], is initially co-located at the origin 66 of the cartesian coordinate system [e.g., at cartesian point (0, 0, 0)]. However, joints 30 of robotic arms 24, 26 are configured to operate in concert to mimic cartesian (e.g., orthogonal) motion to move robotic arms 24 and 26 in horizontal and/or vertical directions relative to rotary stage 18. In other examples, system 10 may include specialized mechanical components, such as guide rails, etc., configured to exclusively move robotic aims 24 and 26 in horizontal and/or vertical directions relative to rotary stage 18.

In some examples, coordinate system 70 defines a secondary cartesian coordinate system centered at detector position 54. For example, either or both of robotic arm 26 and radiation detector 14 may include mechanical components configured to enable radiation detector 14 to horizontally and/or vertically translate along a plane defined by the surface of radiation detector 14. For example, as shown in FIG. 5, a distal end of robotic arm 26 may include a ball screw and nut and servo motor, enabling radiation detector 14 to translate horizontally along horizontal detector axis D and/or vertically along vertical detector axis $D_y$. Enabling detector 14 to move horizontally and/or vertically along a plane located tangentially to the surface of sphere 34 provides at least two advantages.

First, by translating detector 14, image acquisition system 28 may acquire a series of radiographs at different detector positions 54 along the plane defined by the surface of detector 14 (e.g., a plane located tangentially to the surface of sphere 34), wherein the different detector positions are separated by a distance finer than a pixel size of radiation detector 14. Image acquisition system 28 may then assemble the radiographs to form a composite radiograph with finer resolution than the acquired radiographs, as detailed in commonly assigned U.S. Pat. No. 9,459,217.

Second, by translating detector 14, image acquisition system 28 may acquire a series of radiographs at different detector positions 54 along the planed defined by the surface of detector 14 (e.g., a plane located tangentially to the surface of sphere 34). By acquiring radiographs at two or more different detector positions each separated by intervals greater than (e.g., much greater than) the pixel size of radiation detector 14 but less than the detector size, radiation detector 14 may cover a larger area than the physical size of radiation detector 14. Image acquisition system 28 may then numerically "stitch" these digital radiographs together to form a composite radiograph with a greater field of view than the field of view defined by the physical area of detector 14. Further, by acquiring radiographs when radiation detector 14 is at two or more positions separated by intervals smaller than the pixel size, a sub-pixel size sampling effect may be achieved. This technique, in certain optical configurations and with certain types of samples, can be used to generate composite radiographs with finer resolution. These two techniques can be combined in practical use to significantly increase either or both of the imaging field of view and the resolution. Furthermore, these two techniques can further be combined with both conventional volumetric CT and spiral CT techniques to increase a 3-dimensional (3D) reconstructed volume and resolution of object 22.

Figure 6:
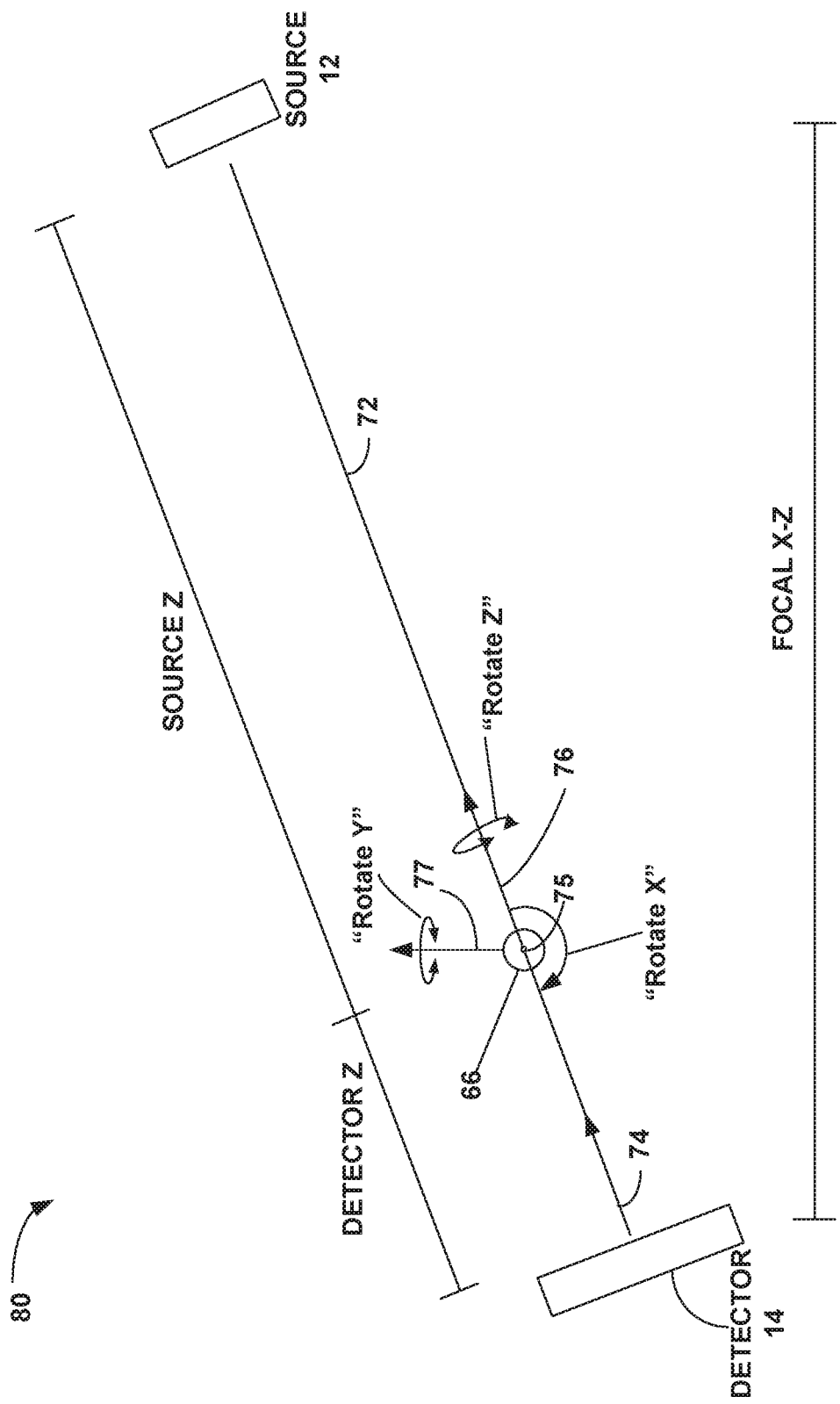
FIG. 6 is a side view of another example NDE system, in accordance with one or more techniques of this disclosure.

As shown in FIGS. 5 and 6, in some examples, system 70 may further include a set of orthogonal x (75), y (77), and z (76) rotation axes. For example, in addition to being horizontally and vertically translatable along reference point cartesian axes x (67), y (68), and z (69), image acquisition system 28 may be configured to cause robotic arms 24 and 26 to commonly rotate both radiation source 12 and detector 14 about these axes. For example, as shown in FIG. 6, a "Rotate X" input command may cause alignment system 28 to rotate both robotic arms 24 and 26 about x rotation axis 75. Similarly, a "Rotate Y" input command may cause alignment system 28 to cause both robotic arms 24 and 26 to rotate about y rotation axis 77. Similarly, as shown in FIG. 6, a "Rotate Z" input command may cause alignment system 28 to cause either or both of source 12 and/or detector 14 to rotate about the z rotation axis 76, or equivalently, the vector 72 (FIG. 6) connecting source 12 to detector 14.

FIG. 5 depicts an additional two degrees of freedom introduced by system 10, specifically, via mechanical properties of rotary stage 18. As described above, rotary stage 18 may be configured to rotate about rotary axis 20. As shown in FIG. 5, rotary stage 18 may also be vertically translatable along rotary axis 20. By simultaneously rotating rotary stage 18 about axis 20, as well as vertically translating rotary stage 18 along axis 20, image acquisition system 28 may generate a helical-type evaluation image of an object 22 placed on stage 18, as detailed in commonly assigned U.S. Pat. No. 9,459,217, filed Apr. 2, 2014.

As shown in FIG. 5, rotary stage 18 may include a first worm screw and set of rails configured to horizontally translate rotary stage 18 in response to a "Rotary Table Left/Right" command. Similarly, rotary stage 18 may include a second worm screw and set of rails configured to horizontally translate rotary stage 18 (e.g., in a forward or backward direction) in response to a "Rotary Table Mag (Magnification)" command, thereby adjusting the image magnification of an object placed on the stage by adjusting the relative distances between radiation source 12, the object, and radiation detector 14. Similarly, image acquisition system 28 may be configured to move (e.g., rotate and/or translate) any mechanical components of system 10 about or along any of the above-described axes while imaging unit 44 captures imagery of object 22 (e.g., causes radiation source 12 to emit radiation toward radiation detector 14 and irradiate object 22).

FIG. 6 is a side view of another example system 80, which may be an example of system 10 of FIGS. 1 and 2, system 60 of FIGS. 3 and 4 and/or system 70 of FIG. 5. When a user of system 80 begins a new object-imaging session, robotic arms 24, 26 (FIG. 1) may initially be in any arbitrary position and/or orientation. Accordingly, system 80 (e.g., image acquisition system 28 of FIG. 2) may be configured to perform an initial alignment operation upon startup of system 80. For example, during the alignment operation, system 80 may control orientation units 46, 48 (FIG. 2) to rotate (e.g., re-orient) source 12 and detector 14 to face each other while maintaining their spatial (e.g., x-y-z) positions. A description of an example alignment operation follows, however, other operations may be used to align source 12 and detector 14.

Figure 7B:
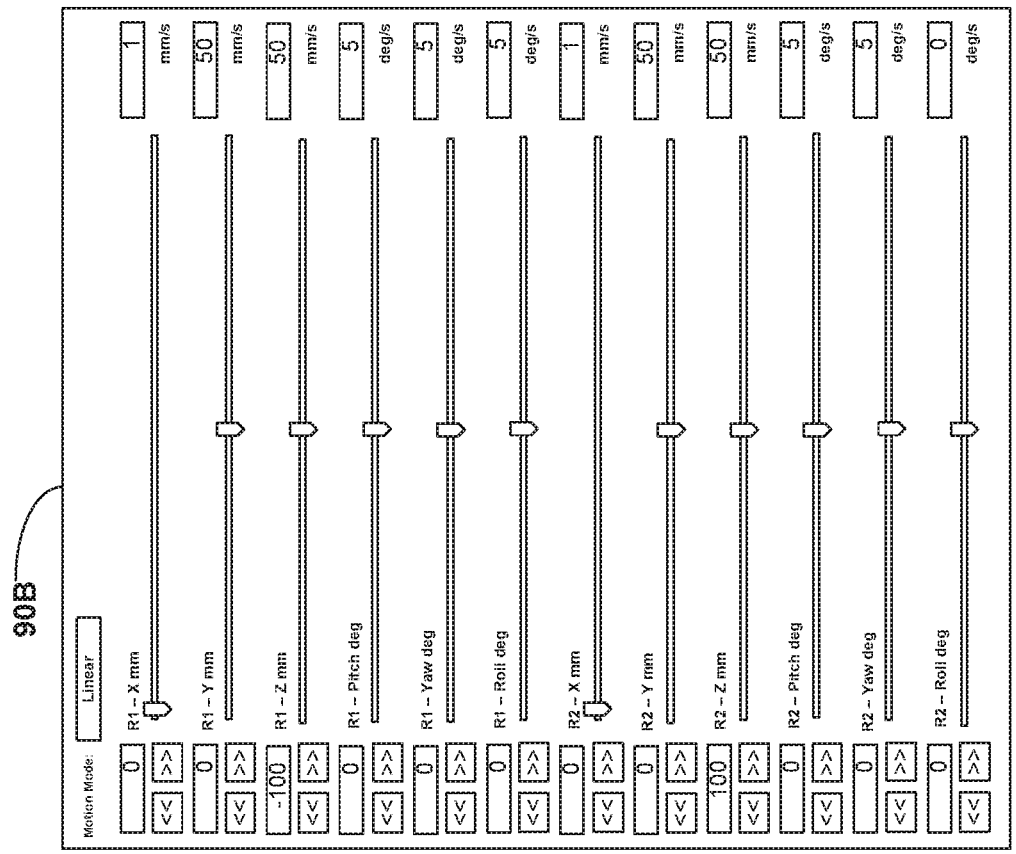
FIGS. 7A and 7B are example graphical user interfaces (GUIs) of an NDE system, in accordance with one or more techniques of this disclosure.
Figure 7A:
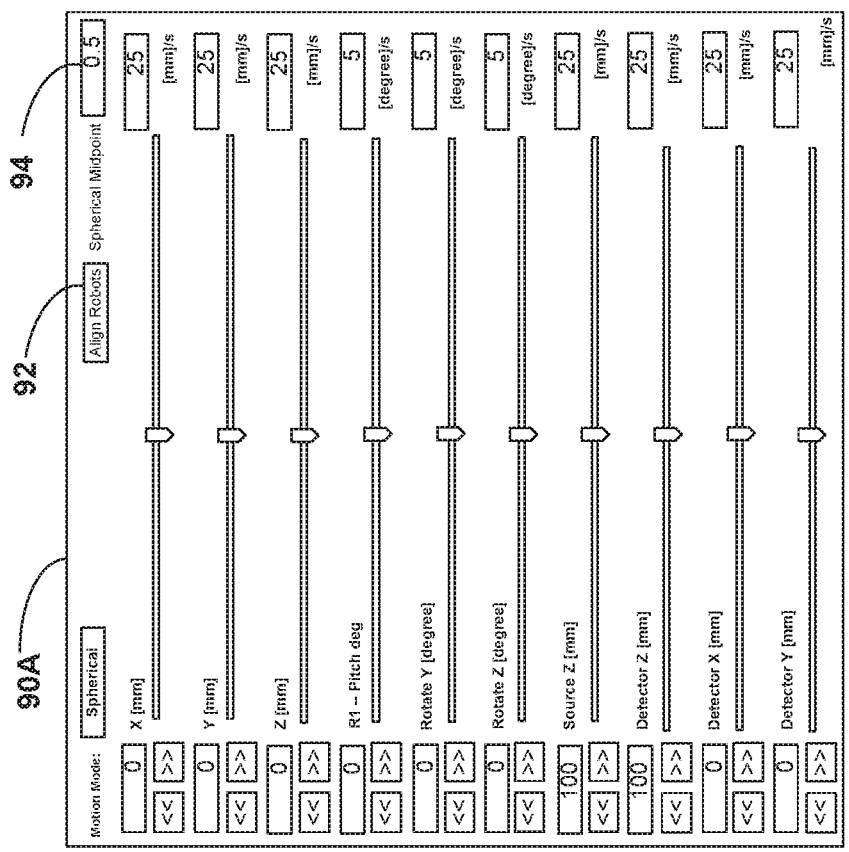

System 80 may receive user input, e.g., via GUI 90A depicted in FIG. 7A, including a user-defined "spherical midpoint" value 94A. The spherical midpoint value may include a number between 0 and 1 that indicates a desired location of reference point 66 (e.g., a center of rotation) along the source-detector vector 72 when system 80 performs the alignment. The user may specify the value for spherical midpoint value 94A, and then actuate the "Align Robots" input button 92 to cause system 80 to perform the alignment. In sonic examples, system 80 may then calculate a fraction of the current distance between source 12 and detector 14 using the spherical midpoint value 94A. System 80 may store this fraction as variable "sourceZ":

sourceZ=length(cource-detector)*midpoint

System 80 may then project this distance onto the X-Z plane 78, thereby effectively removing the y component:

focalXZ=length(source.xz-detector.xz)*midpoint

System 80 may then use the spherical midpoint 94A to determine the location of reference point 66 between source 12 and detector 14:

ref=source+midpoint*(detector-source)

System 80 may then use these two distances and the reference point 66 to calculate the initial x rotation and initial y rotation of the spherical mode:

$$yRot = \sin^{-1}\frac{ref.x - source.x}{focalXC}$$

$$XRot = \sin^{-1}\frac{ref.y - source.y}{sourceZ}$$

System 80 may then determine detectorZ as the remaining length between source 12 and detector 14:

detectorZ=length(source-detector)-sourceZ

System 80 may then set the values of the Z rotation (zRot), detector x offset (detectorX), and detector y offset (detectorY) to zero. System 80 may then send these values to the respective axes in the spherical coordinate system.

Once system 80 has completed the alignment of source 12 and detector 14, system 80 may then determine source and detector positions according to a spherical coordinate system, as shown in FIGS. 3-5. For example, when any spherical motion (e.g., rotation) of arms 24, 26 occurs, system 80 translates current spherical axis values, as shown in GUI 90A of FIG. 7A, to linear coordinates, as shown in GUI 90B of FIG. 7B (e.g., a source position and orientation and a detector position and orientation) that system 80 may then use to move robotic arms 24, 26.

In some examples, the direction of the "y" rotation axis 77 may be considered to be "global," since it is not affected by any rotation within the system. However, in some examples, the "x" rotation axis 75 and the "z" rotation axis 76 may be considered "local" in that they change direction depending on the amount of "v" rotation. For example, rotating the y axis 77 by 45 degrees adjusts the direction of the x rotation axis 75 by 45 degrees, but rotating the x axis 75 by 45 degrees may not change the direction of the y axis 77.

In some examples, system 80 may calculate a detector normal ("detNorm") vector 74 from the spherical x and y rotations. Similarly, unitZ is the unit vector 76 in the z direction (0, 0, 1). xRot, yRot, and zRot are user-defined values from the respective spherical axis:

detNorm=rotate(rotate(unitZ, xRot), yRot)

The detector horizontal ("detHoriz") and detector vertical ("detVert") positional vectors are calculated similarly using all axes of rotation:

detHoriz=rotate(unitX, xRot, yRot, zRot)

detVert rotate(unitY, xRot, yRot, zRot)

System 80 may use these vectors to calculate the 3D linear position of detector 14 as an offset from the spherical reference point 66. DetZ, detX, and detY are user-defined values from the respective spherical axis:

detPos=ref+detZ*detNorm+detX*detHoriz+ detY*detVert

Since detector 14 and source 12 are aligned to detector normal vector 74, system 80 may perform a simplified calculation using the detector normal vector 74 to determine the position of radiation source 12:

sourcePos=ref−sourceZ*detNorm

System 80 calculates the linear x rotation of detector 14 and source 12 from a. projection of the detector normal vector 74:

$$linearXRot = \tan^{-1}\frac{detNorm.y}{length(detNorm.xz)}$$

System 80 may then pass the unchanged spherical y rotation and the unchanged spherical z rotation to the linear rotations of both detector 14 and source 12.

Other examples of system 80 may include graphical user interfaces different from those depicted in FIGS. 7A and 7B (e.g., having more, fewer, or different components). For example, a "simplified" example user interface may enable a user to input a three-dimensional position and orientation vector for each of radiation source 12 and radiation detector 14. The three-dimensional position and orientation vectors may be received in cartesian (x, y, z) notation or in spherical (R, θ, φ) notation. A more complex example user interface may enable a user to control each joint 30 (FIG. 1) of robotic arms 24, 26, or similar kinematics enabling more precise control over joints 30.

In some examples, a user interface of system 80 may include a graphical representation of system 80 based on the received input. For example, the user interface may display a three-dimensional representation of the positions and orientations of radiation source 12, radiation detector 14, radiation beam 16, object 22, stage 18, and center 33 relative to each other. The user interface may provide user input mechanisms allowing the user to rotate the perspective of the graphical representation. In some examples, system 80 may be configured to display a physical representation of imaginary center 33 of the spherical coordinate system. For example, system 80 may include a laser or LEDs configured to illuminate a position within housing 11 (FIG. 2) immediately above or underneath center 33 of the corresponding spherical coordinate system. In other examples, system 80 may include a mechanical indicator of center 33, configured to move within housing 11 as system 80 moves the imaginary center 33 (e.g., commonly moves source 12 and detector 14 relative to the rest of system 80).

Figure 8:
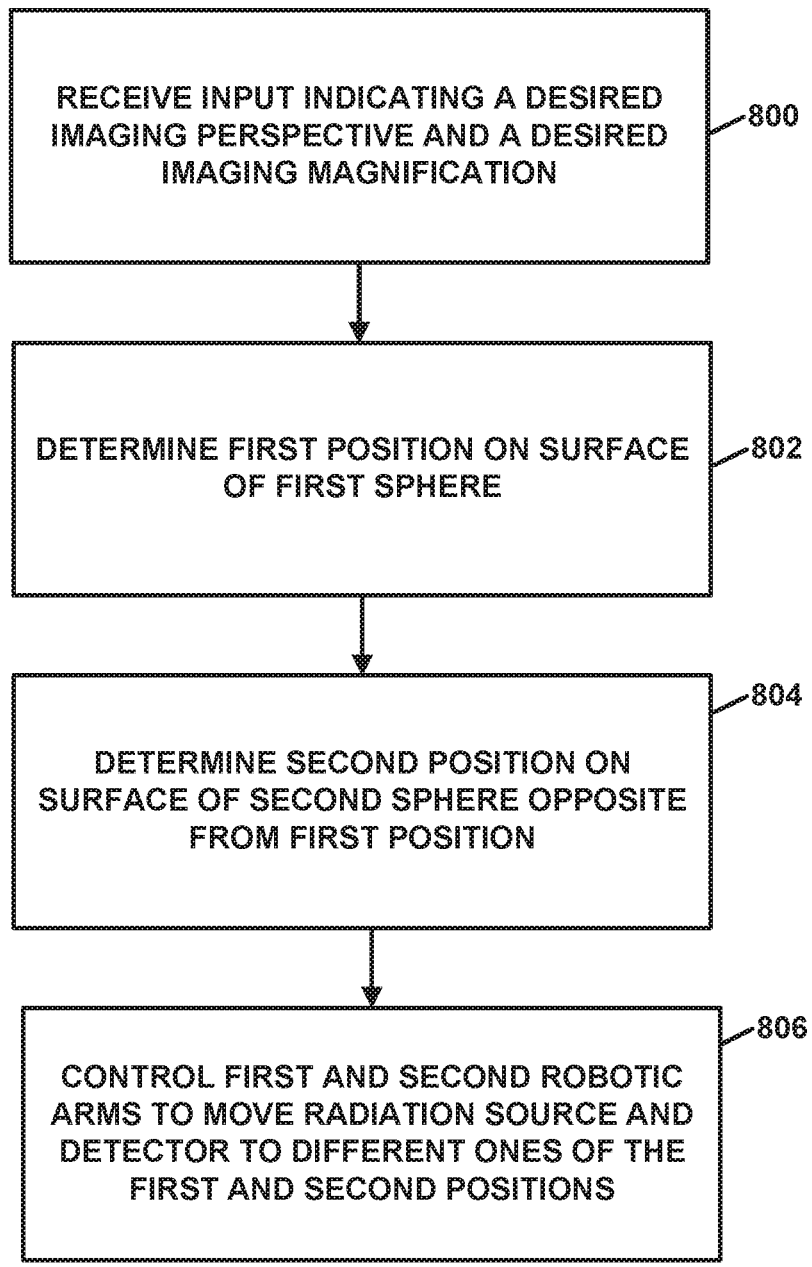
FIG. 8 is a flowchart illustrating an example operation of an NDE system, in accordance with one or more techniques of this disclosure.

FIG. 8 is a flowchart illustrating an example operation of a non-destructive evaluation system, such as an industrial CT system or metrology system, in accordance with one or more techniques of this disclosure. The example operation of FIG. 8 is explained with reference to the example system 10 of FIGS. 1 and 2. However, the example operation of FIG. 8 is not so limited.

In the example of FIG. 8, image acquisition system 28 (e.g., a computing device of system 10) receives input indicating a desired imaging perspective and/or a desired imaging magnification for x-ray imaging of an object 22 that may be placed on a rotary stage 18 of system 10 (800). The input may include direct (e.g., real-time) user input, or in some examples, a set of predetermined instructions stored within a file that is imported or otherwise received by image acquisition system 28.

Based on the received input, image acquisition system 28 determines (e.g., generates, selects, calculates, and/or assigns) a source position 52 for a radiation source 12 and a detector position 54 for a radiation detector 14. In some examples, image acquisition system 28 may determine source position 52 first, and then determine detector position 54 based on (e.g., opposite from) source position 52. In other examples, image acquisition system 28 may determine detector position 54 first, and then determine source position 52 based on (e.g., opposite from) detector position 54. In other examples, image acquisition system 28 may independently determine source position 52 and detector position 54 based on the received input.

In some examples, image acquisition system 28 may determine, based on the input, a first position (e.g., source position 52) located on a surface of a first imaginary sphere located within a spherical coordinate system (802). Similarly, image acquisition system 28 may determine a second position e.g., detector position 54) located on a surface of a second imaginary sphere located within the same spherical coordinate system (804). The second position is located opposite a center of the spherical coordinate system from the first position. Each of source position 52 and detector position 54 may be described by three spherical coordinates, (R,θ, φ) relative to the center 33 of the spherical coordinate system. In some examples, image acquisition system 28 may further determine and control a source orientation 62 and a detector orientation 64 in order to direct a radiation beam 16 from ra.diation source 12 toward a surface of radiation detector 14.

Once image acquisition system 28 has determined a first position on a surface of a first imaginary sphere, and a second position on a surface of a second imaginary sphere, image acquisition system 28 (e.g., alignment unit 42 of image acquisition system 28) controls robotic arms 24 and 26 to move radiation source 12 and radiation detector 14 to different ones of the first position and the second position (806).

Once the radiation source 12 and the radiation detector 14 are in position, image acquisition system 28 (e.g., imaging unit 44 of image acquisition unit 28) may cause object 22 to be imaged, e.g., by causing radiation source 12 to emit radiation beam 16 through (e.g., irradiate) object 22 and onto radiation detector 14.

The following paragraphs provide additional example techniques of this disclosure.

Example 1: In some examples, a system for non-destructive evaluation of an object includes a first robotic arm; a radiation source coupled to the first robotic arm, the radiation source configured to emit ra.diation; a second robotic arm; a radiation detector coupled to the second robotic arm, the radiation detector configured to measure the radiation emitted by the radiation source; a stage configured to support the object for non-destructive evaluation; and a control unit configured to: determine, based on input, a first position located on a first surface of a first sphere within a spherical coordinate system; determine, based on the input, a second position located on a second surface of a second sphere within the spherical coordinate system, wherein the second position is located opposite a center of the spherical coordinate system from the first position; and control a motion of the first robotic arm and the second robotic arm such that the radiation source and the radiation detector move to different ones of the first position and the second position.

Example 2: in some examples of the system of Example 1, the control unit s further configured to receive the input, wherein the input indicates an imaging angle for evaluation of the object; and determine, based on the imaging angle, the first position and the second position.

Example 3: In some examples of the system of Example 1 or Example 2, the control unit is further configured to control a source orientation of the radiation source such that the radiation is aimed at the detector from the first position or the second position; and control a detector orientation of the detector such that the detector is aimed at the radiation source from the first position or the second position.

Example 4: In some examples of the system of any of Examples 1-3, the control unit is further configured to receive the input, wherein the input indicates a magnification for evaluation of the object; determine, based on the magnification, a source position defining a source radius; anddetermine, based on the magnification, a detector position defining a detector radius, wherein the sum of the detector radius and the source radius divided by the source radius equals the magnification, and wherein the source position and the detector position are different ones of the first position and the second position.

Example 5: In some examples of the system of any of Examples 1-4, the control unit is further configured to cause the radiation source to irradiate the object in response to controlling the motions of the first robotic arm and the second robotic arm.

Example 6: In some examples of the system of any of Examples 1-5, the radiation detector includes a protective plate having at least one pressure sensor configured to disable the motion of the second robotic ann in response to the pressure sensor detecting contact with an item.

Example 7: In some examples of the system of any of Examples 1-6, the control unit is further configured to acquire a series of radiographs at different detector positions along a plane located tangentially to the second surface of the second sphere within the spherical coordinate system, the different detector positions separated by a distance finer than a pixel size of the radiation detector; and assemble the radiographs to form a composite radiograph with finer resolution than the acquired radiographs.

Example 8: In some examples of the system of any of Examples 1-7, the control unit is further configured to acquire a series of radiographs at different detector positions along a plane located tangentially to the second surface of the second sphere within the spherical coordinate system, the different detector positions separated by a distance greater than a pixel size of the radiation detector but less than a physical size of the detector; and assemble the radiographs to form a composite radiograph having a larger area than the physical size of the detector.

Example 9: In some examples, a computer-readable storage medium includes program instructions that, when executed by a system for non-destructive evaluation of an object placed on a stage, cause the system to determine, based on input, a first position located on a first surface of a first sphere within a spherical coordinate system; determine, based on the input, a second position located on a second surface of a second sphere within the spherical coordinate system, wherein the second position is located opposite a center of the spherical coordinate system from the first position; and control a motion of a first robotic arm and a motion of a second robotic arm such that a radiation source and a radiation detector move to different ones of the first position and the second position, Example 10: In some examples of the computer-readable medium of Example 9, the input indicates an imaging angle for evaluation of the object; and the execution of the program instructions further causes the system to determine, based on the imaging angle, the first position and the second position.

Example 11: In some examples of the computer-readable medium of Example 9 or Example 10, the execution of the program instructions causes the system to control a source orientation of the radiation source such that the radiation is aimed at the detector from a source position; and control a detector orientation of the detector such that the detector is aimed at the radiation source from a detector position, wherein the source position and the detector position comprise different ones of the first position and the second position.

Example 12 In some examples of the computer-readable medium of any of Examples 9-11, the execution of the program instructions causes the system to receive the input, wherein the input indicates a magnification for evaluation of the object; determine, based on the magnification, a source position defining a source radius; and determine, based on the magnification, a detector position defining a detector radius, wherein the sum of the detector radius and the source radius divided by the source radius equals the magnification, and wherein the source position and the detector position comprise different ones of the first position and the second position.

Example 13: In some examples of the computer-readable medium of any of Examples 9-12, the execution of the program instructions further causes the radiation source to irradiate the object in response to controlling the motions of the source robotic arm and the detector robotic arm.

Example 14: In some examples of the computer-readable medium of any of Examples 9-13, the execution of the program instructions further causes the system to acquire a series of radiographs at different detector positions along a plane located tangentially to the second surface of the second sphere within the spherical coordinate system, the different detector positions separated by a distance finer than a pixel size of the detector, and assemble the radiographs to form a composite radiograph with finer resolution than the acquired radiographs, Example 15: In some examples, a method includes determining, based on input into a system for non-destructive evaluation of an object placed on a stage, a first position located on a first surface of a first sphere within a spherical coordinate system; determining, based on the input, a second position located on a second surface of a second sphere within the spherical coordinate system, wherein the second position is located opposite a center of the spherical coordinate system from the first position; and controlling a motion of a first robotic arm and a motion of a second robotic arm such that a radiation source and a radiation detector move to different ones of the first position and the second position.

Example 16: In some examples of the method of Example 15, the input indicates an imaging angle for evaluation of the object, and the method further includes determining, based on the imaging angle, a source position and a detector position, wherein the source position and the detector position include different ones of the first position and the second position.

Example 17: In some examples of the method of Example 15 or Example 16, the method further includes controlling a source orientation of the radiation source such that the radiation is aimed at the detector from a source position; and controlling a detector orientation of the detector such that the detector is aimed at the radiation source from a detector position, wherein the source position and the detector position include different ones of the first position and the second position.

Example 18: in some examples of the method of any of Examples 15-17, the method further includes receiving the input, wherein the input indicates a magnification for evaluation of the object; determining, based on the magnification, a source position defining a source radius; and determining, based on the magnification, a detector position defining a detector radius, wherein the sum of the detector radius and the source radius divided by the source radius equals the magnification, and wherein the source position and the detector position include different ones of the first position and the second position.

Example 19: In some examples of the method of any of Examples 15-18, the method further includes causing the radiation source to irradiate the object in response to controlling the motions of the first robotic arm and the second robotic arm.

Example 20: In some examples of the method of any of Examples 15-19, the method further includes acquiring a series of radiographs at different detector positions along a plane located tangentially to the second surface of the second sphere within the spherical coordinate system, the different detector positions separated by a distance finer than a pixel size of the detector, and assembling the radiographs to form a composite radiograph with finer resolution than the acquired radiographs.

Various examples have been described. These and other examples are within the scope of the following claims.

What is claimed is:

1. A system for non-destructive evaluation of an object comprising:
   a first robotic arm;
   a radiation source coupled to the first robotic arm, the radiation source configured to emit radiation;
   a second robotic arm;
   a radiation detector coupled to the second robotic arm, the radiation detector configured to measure the radiation emitted by the radiation source;
   a stage configured to support the object for non-destructive evaluation; and
   a control unit configured to:
      receive input identifying an imaging angle for evaluation of the object;
      determine, based on the imaging angle, a first position located on a first surface of a first sphere within a spherical coordinate system;
      determine, based on the imaging angle, a second position located on a second surface of a second sphere within the spherical coordinate system, wherein the second position is located opposite a center of the spherical coordinate system from the first position; and
      control a motion of the first robotic arm and the second robotic arm such that the radiation source and the radiation detector move to different ones of the first position and the second position.

2. The system of claim 1, the control unit further configured to:
   control a source orientation of the radiation source such that the radiation is aimed at the detector from the first position or the second position; and
   control a detector orientation of the detector such that the detector is aimed at the radiation source from the first position or the second position.

3. The system of claim 1, wherein:
   the first position is a position of the radiation source, the second position is a position of the radiation detector, the control unit further configured to:
      receive the input, wherein the input indicates a magnification for evaluation of the object;
      as part of determining the first position, determine, based on the magnification, a source radius, wherein the source radius is a radius component of spherical coordinates of the first position; and
      as part of determining the second position, determine, based on the magnification, a detector radius, wherein:
         the detector radius is a radius component of spherical coordinates of the second position, and
         the sum of the detector radius and the source radius divided by the source radius equals the magnification, and wherein the source position and the detector position are different ones of the first position and the second position.

4. The system of claim 1, wherein the control unit is further configured to cause the radiation source to irradiate the object in response to controlling the motions of the first robotic arm and the second robotic arm.

5. The system of claim 1, wherein the radiation detector comprises a protective plate having at least one pressure sensor configured to disable the motion of the second robotic arm in response to the pressure sensor detecting contact with an item.

6. The system of claim 1, wherein the control unit is further configured to:
   acquire a series of radiographs at different detector positions along a plane located tangentially to the second surface of the second sphere within the spherical coordinate system, the different detector positions separated by a distance finer than a pixel size of the radiation detector; and
   assemble the radiographs to form a composite radiograph with finer resolution than the acquired radiographs.

7. The system of claim 1, wherein the control unit is further configured to:
   acquire a series of radiographs at different detector positions along a plane located tangentially to the second surface of the second sphere within the spherical coordinate system, the different detector positions separated by a distance greater than a pixel size of the radiation detector but less than a physical size of the detector; and
   assemble the radiographs to form a composite radiograph having a larger area than the physical size of the detector.

8. A computer-readable storage medium including program instructions that, when executed by a system for non-destructive evaluation of an object placed on a stage, cause the system to:
   receive input identifying an imaging angle for evaluation of the object;
   determine, based on the imaging angle, a first position located on a first surface of a first sphere within a spherical coordinate system;
   determine, based on the imaging angle, a second position located on a second surface of a second sphere within the spherical coordinate system, wherein the second position is located opposite a center of the spherical coordinate system from the first position; and control a motion of a first robotic arm and a motion of a second robotic arm such that a radiation source and a radiation detector move to different ones of the first position and the second position.

9. The computer-readable storage medium of claim 8, wherein the execution of the program instructions further causes the system to:

control a source orientation of the radiation source such that the radiation is aimed at the detector from a source position; and control a detector orientation of the detector such that the detector is aimed at the radiation source from a detector position, wherein the source position and the detector position comprise different ones of the first position and the second position.

10. The computer-readable storage medium of claim 8, the first position is a position of the radiation source, the second position is a position of the radiation detector, wherein the execution of the program instructions further causes the system to:

receive the input, wherein the input indicates a magnification for evaluation of the object;

as part of determining the first position, determine, based on the magnification, a source radius, wherein the source radius is a radius component of spherical coordinates of the first position; and as part of determining the second position, determine, based on the magnification, a detector radius, wherein:

the detector radius is a radius component of spherical coordinates of the second position, and the sum of the detector radius and the source radius divided by the source radius equals the magnification, and wherein the source position and the detector position are different ones of the first position and the second position.

11. The computer-readable storage medium of claim 8, wherein the execution of the program instructions further causes the radiation source to irradiate the object in response to controlling the motions of the source robotic arm and the detector robotic arm.

12. The computer-readable storage medium of claim 8, wherein the execution of the program instructions further causes the system to:

acquire a series of radiographs at different detector positions along a plane located tangentially to the second surface of the second sphere within the spherical coordinate system, the different detector positions separated by a distance finer than a pixel size of the detector, and assemble the radiographs to form a composite radiograph with finer resolution than the acquired radiographs.

13. A method comprising:

receive input identifying an imaging angle for non-destructive evaluation of an object placed on a stage;

determining, based on the imaging angle, a first position located on a first surface of a first sphere within a spherical coordinate system;

determining, based on the imaging angle, a second position located on a second surface of a second sphere within the spherical coordinate system, wherein the second position is located opposite a center of the spherical coordinate system from the first position; and controlling a motion of a first robotic arm and a motion of a second robotic arm such that a radiation source and a radiation detector move to different ones of the first position and the second position.

14. The method of claim 13, further comprising:

controlling a source orientation of the radiation source such that the radiation is aimed at the detector from a source position; and controlling a detector orientation of the detector such that the detector is aimed at the radiation source from a detector position, wherein the source position and the detector position comprise different ones of the first position and the second position.

15. The method of claim 13, wherein the first position is a position of the radiation source, the second position is a position of the radiation detector, the method further comprising:

receiving the input, wherein the input indicates a magnification for evaluation of the object;

as part of determining the first position, determining, based on the magnification, a source radius, wherein the source radius is a radius component of spherical coordinates of the first position; and as part of determining the second position, determining, based on the magnification, a detector radius, wherein:

the detector radius is a radius component of spherical coordinates of the second position, and the sum of the detector radius and the source radius divided by the source radius equals the magnification, and wherein the source position and the detector position are different ones of the first position and the second position.

16. The method of claim 13, further comprising causing the radiation source to irradiate the object in response to controlling the motions of the first robotic arm and the second robotic arm.

17. The method of claim 13, further comprising:

acquiring a series of radiographs at different detector positions along a plane located tangentially to the second surface of the second sphere within the spherical coordinate system, the different detector positions separated by a distance finer than a pixel size of the detector, and assembling the radiographs to form a composite radiograph with finer resolution than the acquired radiographs.

18. The system of claim 1, wherein the control unit is further configured to:

translate the spherical coordinates of the first position and the spherical coordinates of the second position to linear coordinates.

* * * * *